US012376850B2

(12) United States Patent
Koka et al.

(10) Patent No.: US 12,376,850 B2
(45) Date of Patent: Aug. 5, 2025

(54) SURGICAL STAPLE

(71) Applicant: Medline Industries, LP, Northfield, IL (US)

(72) Inventors: Dinesh Koka, Winter Park, FL (US); Samuel Nader, Arlington Heights, IL (US); Ryan Niver, Glenview, IL (US); Natan Pheil, Highland Park, IL (US); Wesley Reed, Libertyville, IL (US)

(73) Assignee: Medline Industries, LP, Northfield, IL (US)

( * ) Notice: Subject to any disclaimer, the term of this patent is extended or adjusted under 35 U.S.C. 154(b) by 229 days.

(21) Appl. No.: 18/213,230

(22) Filed: Jun. 22, 2023

(65) Prior Publication Data

US 2024/0423612 A1 Dec. 26, 2024

(51) Int. Cl.
*A61B 17/064* (2006.01)
*A61B 17/068* (2006.01)
*A61B 17/56* (2006.01)

(52) U.S. Cl.
CPC ...... *A61B 17/0642* (2013.01); *A61B 17/0682* (2013.01); *A61B 2017/0641* (2013.01); *A61B 2017/0645* (2013.01); *A61B 2017/564* (2013.01)

(58) Field of Classification Search
CPC ........ A61B 2017/0641; A61B 17/0642; A61B 2017/0645; A61B 17/0682; A61B 2017/564
See application file for complete search history.

(56) References Cited

U.S. PATENT DOCUMENTS

| | | | |
|---|---|---|---|
| 294,777 | A | 3/1884 | Forbes |
| 324,126 | A | 8/1885 | Gay |
| D28,350 | S | 3/1898 | Reuter |
| D29,472 | S | 10/1898 | Hughes et al. |
| 1,257,807 | A | 2/1918 | Carrell |
| 1,354,737 | A | 10/1920 | Frisk |
| 1,639,530 | A | 8/1927 | Payson |
| 2,067,359 | A | 1/1937 | Tumminello |
| 2,174,708 | A | 10/1939 | Sears |
| 3,154,999 | A | 11/1964 | Stewart |

(Continued)

FOREIGN PATENT DOCUMENTS

| | | |
|---|---|---|
| EP | 0127994 | 12/1984 |
| FR | 2628312 | 9/1989 |

(Continued)

OTHER PUBLICATIONS

Memometal Inc. USA, Easy Clip SI brochure, Aug. 12, 2009.

(Continued)

*Primary Examiner* — Larry E Waggle, Jr.
(74) *Attorney, Agent, or Firm* — Fitch, Even, Tabin & Flannery LLP

(57) ABSTRACT

A surgical staple is provided having a bridge and at least a first leg and a second leg. The bridge has a first end and a second end. The surgical staple has a first extension of the bridge adjacent the first end of the bridge and extending on an opposite side of the first leg relative to the second leg and a second extension of the bridge adjacent the second end of the bridge and extending on an opposite side of the second leg relative to the first leg. The bridge may also have a waisted or reduced width mid-section.

18 Claims, 14 Drawing Sheets

(56) References Cited

U.S. PATENT DOCUMENTS

| | | |
|---|---|---|
| 3,316,794 A | 5/1967 | Dixon |
| 3,564,663 A | 2/1971 | Roberts |
| 3,584,347 A | 6/1971 | Klenz |
| 3,787,608 A | 1/1974 | Colby |
| 3,821,919 A | 7/1974 | Knohl |
| 3,824,995 A | 7/1974 | Getscher |
| 3,940,844 A | 3/1976 | Colby |
| 3,960,147 A | 6/1976 | Murray |
| D243,365 S | 2/1977 | Cross |
| 4,263,903 A | 4/1981 | Griggs |
| 4,454,875 A | 6/1984 | Pratt |
| D281,814 S | 12/1985 | Pratt |
| 4,565,193 A | 1/1986 | Streli |
| 4,570,623 A | 2/1986 | Ellison |
| 4,592,346 A | 6/1986 | Jurgutis |
| D286,442 S | 10/1986 | Korthoff |
| 4,799,481 A | 1/1989 | Transue |
| 4,848,328 A | 7/1989 | Laboureau |
| 5,179,964 A | 1/1993 | Cook |
| 5,263,973 A | 11/1993 | Cook |
| 5,449,359 A | 9/1995 | Groiso |
| 5,454,814 A | 10/1995 | Comte |
| 5,662,655 A | 9/1997 | Laboureau |
| 5,674,222 A | 10/1997 | Berger |
| 5,785,713 A | 7/1998 | Jobe |
| 5,853,414 A | 12/1998 | Groiso |
| 5,941,890 A | 8/1999 | Voegele |
| 6,001,110 A | 12/1999 | Adams |
| 6,066,142 A | 5/2000 | Serbousek |
| 6,120,511 A | 9/2000 | Chan |
| 6,187,009 B1 | 2/2001 | Herzog |
| 6,325,805 B1 | 12/2001 | Ogilvie |
| 6,336,928 B1 | 1/2002 | Guerin |
| 6,401,306 B1 | 6/2002 | Hanten |
| 6,652,592 B1 | 11/2003 | Grooms |
| 6,767,356 B2 | 7/2004 | Kanner |
| 6,773,437 B2 | 8/2004 | Ogilvie |
| 7,108,697 B2 | 9/2006 | Mingozzi |
| D572,363 S | 7/2008 | Menn |
| D587,370 S | 2/2009 | Coillard-Lavirotte |
| D596,294 S | 7/2009 | Coillard-Lavirotte |
| 7,722,610 B2 | 5/2010 | Viola |
| 7,794,475 B2 | 9/2010 | Hess |
| 7,824,426 B2 | 11/2010 | Racenet |
| 8,021,389 B2 | 9/2011 | Molz, IV |
| 8,360,297 B2 | 1/2013 | Shelton, IV |
| 8,366,748 B2 | 2/2013 | Kleiner |
| 8,393,517 B2 | 3/2013 | Milo |
| 8,584,853 B2 | 11/2013 | Knight |
| 8,596,514 B2 | 12/2013 | Miller |
| 8,679,154 B2 | 3/2014 | Smith |
| D705,930 S | 5/2014 | Cheney |
| 8,720,766 B2 | 5/2014 | Hess |
| D707,357 S | 6/2014 | Cheney |
| 8,808,325 B2 | 8/2014 | Hess |
| D728,103 S | 4/2015 | Katchis |
| 9,039,737 B2 | 5/2015 | Vold |
| 9,198,769 B2 | 12/2015 | Perrow |
| 9,254,180 B2 | 2/2016 | Huitema |
| 9,295,463 B2 | 3/2016 | Viola |
| 9,339,268 B2 | 5/2016 | Fox |
| 9,402,624 B1 | 8/2016 | Scott |
| 9,433,452 B2 | 9/2016 | Weiner |
| 9,463,260 B2 | 10/2016 | Stopek |
| 9,486,212 B2 | 11/2016 | Miller |
| D780,311 S | 2/2017 | Cheney |
| 9,743,926 B2 | 8/2017 | Fox |
| 9,855,036 B2 | 1/2018 | Palmer |
| 9,901,338 B2 | 2/2018 | Anderson |
| D826,405 S | 8/2018 | Shelton, IV |
| 10,058,366 B2 | 8/2018 | Bouduban |
| 10,064,619 B2 | 9/2018 | Palmer |
| 10,064,623 B2 | 9/2018 | Soutorine |
| 10,085,743 B2 | 10/2018 | Roedl |
| 10,105,134 B2 * | 10/2018 | Biedermann ........ A61B 17/083 |
| 10,117,647 B2 | 11/2018 | Cheney |
| 10,130,358 B2 | 11/2018 | Palmer |
| 10,166,022 B2 | 1/2019 | Early |
| D840,035 S | 2/2019 | Weiner |
| 10,238,382 B2 | 3/2019 | Terrill |
| 10,307,156 B1 | 6/2019 | Blair |
| D857,199 S | 8/2019 | Cheney |
| 10,610,218 B2 | 4/2020 | Palmer et al. |
| D886,299 S | 6/2020 | Cundiff |
| D895,113 S | 9/2020 | Blair |
| 10,779,816 B2 | 9/2020 | Goldstein |
| 10,820,902 B2 | 11/2020 | Cheney |
| 10,874,389 B2 | 12/2020 | Biedermann |
| 10,918,484 B2 | 2/2021 | Ellington et al. |
| 10,945,725 B2 | 3/2021 | Hollis |
| 10,987,101 B2 | 4/2021 | Ducharme |
| 11,000,323 B2 | 5/2021 | Stamp |
| 11,006,949 B2 | 5/2021 | Daniel |
| 11,020,110 B1 | 6/2021 | Blair |
| 11,090,043 B2 | 8/2021 | Biedermann |
| 11,116,499 B1 * | 9/2021 | Blair ............... A61B 17/0644 |
| 11,278,278 B2 | 3/2022 | Biedermann |
| 11,284,886 B2 | 3/2022 | Hartdegen |
| D957,636 S | 7/2022 | Blair |
| 11,553,952 B2 | 1/2023 | Hammann |
| 11,596,398 B2 | 3/2023 | Wahl |
| 11,642,124 B2 | 5/2023 | Maclure et al. |
| 11,653,913 B2 | 5/2023 | Goldstein et al. |
| 11,684,359 B2 | 6/2023 | Biedermann |
| 11,911,036 B2 | 2/2024 | Reed |
| D1,017,038 S | 3/2024 | Bushko |
| 11,937,819 B2 | 3/2024 | Pheil |
| 2003/0225423 A1 | 12/2003 | Huitema |
| 2004/0193188 A1 | 9/2004 | Francese |
| 2005/0021035 A1 | 1/2005 | Groiso |
| 2005/0288707 A1 | 12/2005 | De Canniere |
| 2006/0058802 A1 | 3/2006 | Kofoed |
| 2007/0233113 A1 | 10/2007 | Kaelblein |
| 2007/0270906 A1 | 11/2007 | Molz |
| 2007/0276388 A1 | 11/2007 | Robertson |
| 2008/0147068 A1 | 6/2008 | Hashimoto |
| 2009/0005809 A1 | 1/2009 | Hess |
| 2011/0022099 A1 | 1/2011 | Ashman |
| 2013/0231667 A1 | 9/2013 | Taylor |
| 2013/0345752 A1 | 12/2013 | Hendren |
| 2014/0276830 A1 | 9/2014 | Cheney |
| 2014/0277516 A1 | 9/2014 | Miller |
| 2014/0358187 A1 | 12/2014 | Taber |
| 2015/0133940 A1 | 5/2015 | Palmer |
| 2015/0313592 A1 | 11/2015 | Coillard-Lavirotte |
| 2017/0000482 A1 | 1/2017 | Averous |
| 2017/0252036 A1 | 9/2017 | Palmer et al. |
| 2018/0271521 A1 | 9/2018 | Wahl |
| 2018/0344316 A1 | 12/2018 | Palmer |
| 2019/0046182 A1 | 2/2019 | Krumme |
| 2019/0069892 A1 | 3/2019 | Biedermann |
| 2019/0105040 A1 | 4/2019 | Gordon |
| 2019/0115040 A1 | 4/2019 | Kamdar et al. |
| 2020/0000046 A1 | 1/2020 | Orschulik |
| 2020/0038076 A1 * | 2/2020 | Amis ............... A61B 17/808 |
| 2020/0046345 A1 | 2/2020 | Zink |
| 2021/0298748 A1 | 9/2021 | Campbell |
| 2021/0330324 A1 | 10/2021 | Biedermann |
| 2021/0386422 A1 | 12/2021 | Maclure |
| 2022/0211368 A1 | 7/2022 | Hartdegen |
| 2023/0000488 A1 | 1/2023 | Palmer |
| 2023/0060073 A1 | 2/2023 | Niver |
| 2023/0172647 A1 * | 6/2023 | Knight ............ A61B 17/0642 606/331 |
| 2023/0200809 A1 | 6/2023 | Wahl |

FOREIGN PATENT DOCUMENTS

| | | |
|---|---|---|
| FR | 2694696 | 2/1994 |
| FR | 3023468 | 1/2016 |
| GB | 793126 | 4/1958 |
| IL | 64726 | 2/1985 |

(56) References Cited

FOREIGN PATENT DOCUMENTS

| WO | 9616603 | 6/1996 |
| WO | 2006077878 | 7/2006 |
| WO | 201288575 | 7/2012 |

OTHER PUBLICATIONS

Stryker, EasyClip Osteosynthesis Compression Staples brochure, bearing a copyright date of 2015.
U. Rethnam et al., "Mechanical Characteristics of Three Staples Commonly Used in Foot Surgery," Journal of Foot and Ankle Research (Feb. 25, 2009).

* cited by examiner

SURGICAL STAPLE

FIELD

A surgical staple is described herein and, in particular, a surgical staple having a bridge and plurality of legs.

BACKGROUND

Surgical staples are commonly used for joining or fusing two bones or bone pieces together. The staples may cross a joint, fracture or osteotomy. For example, staples can be used to fuse metatarsal phalangeal (MTP) joints to relieve pain. By way of another example, staples can be used in a Lapidus procedure to fuse the joint between the first metatarsal bone and the medial cuneiform. Surgical staples can have geometries that range from very simple, with a bridge and several legs, to complex, such as having protuberances for use with insertion. However, protuberances can cause tissue irrigation following implanting of the surgical staple.

DETAILED DESCRIPTION

As described herein and shown in FIGS. 1-28, a surgical staple 100 and associated tools and methods are disclosed for use in, for example, securing adjacent bones using the surgical staple 100. As used herein, adjacent bones can also include bon e pieces of the same bone that require fusion.

Figure 1:
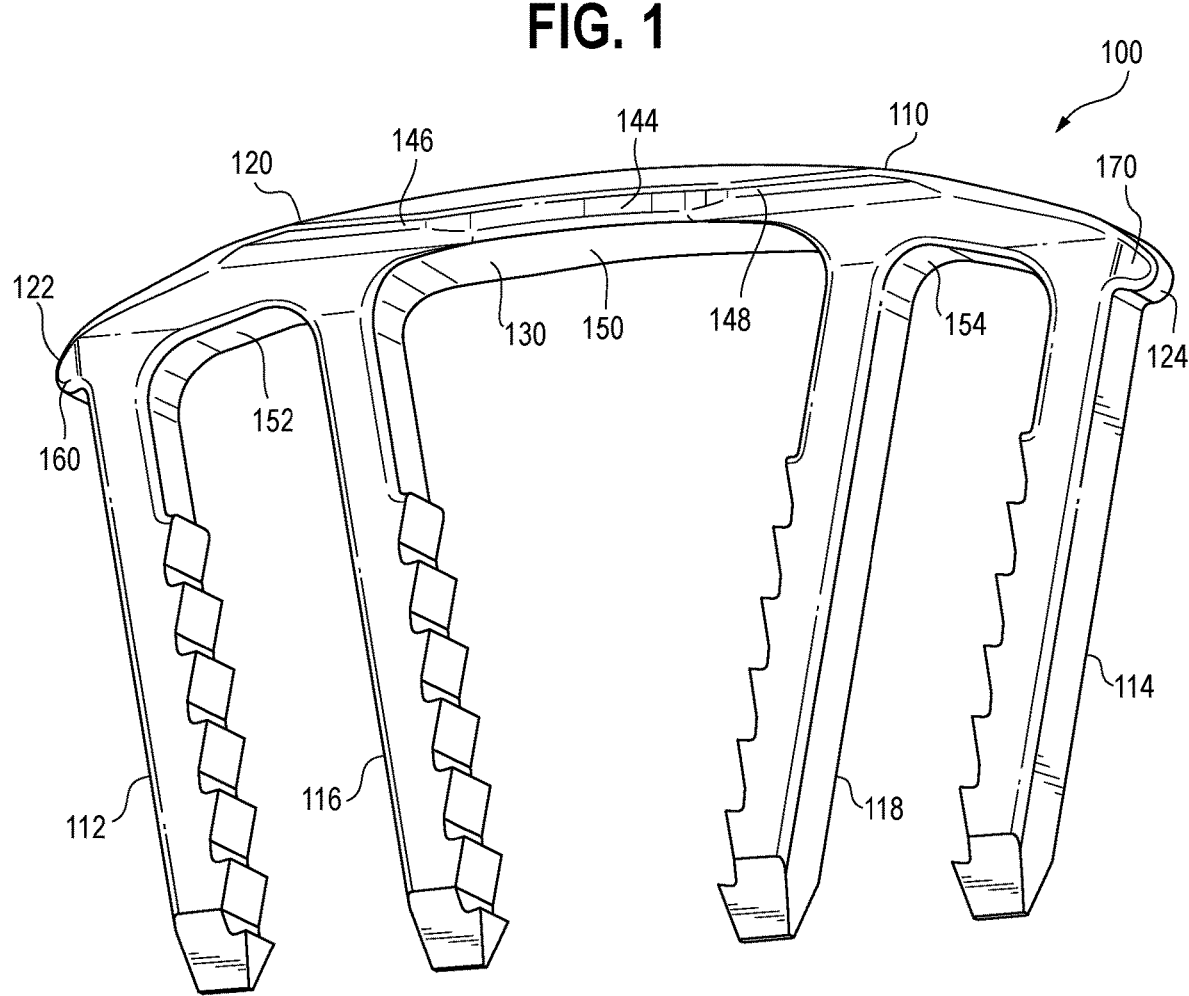
FIG. 1 is a perspective view of an embodiment of a surgical staple suitable for insertion into one or more bones or bone pieces, the surgical staple having a bridge, a plurality of legs, a first extension and a second extension, the surgical staple being shown in a relaxed configuration.
Figure 2:
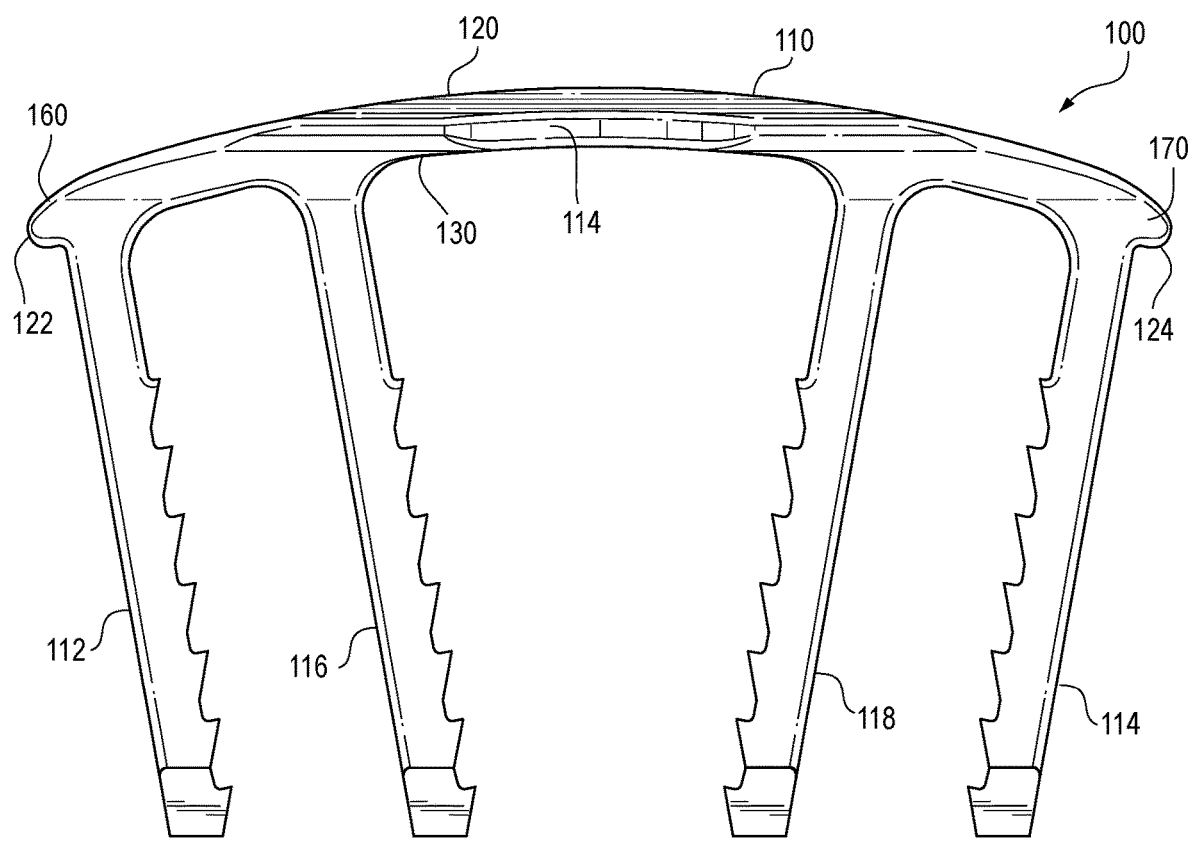
FIG. 2 is a front elevation view of the surgical staple of FIG. 1.
Figure 3:
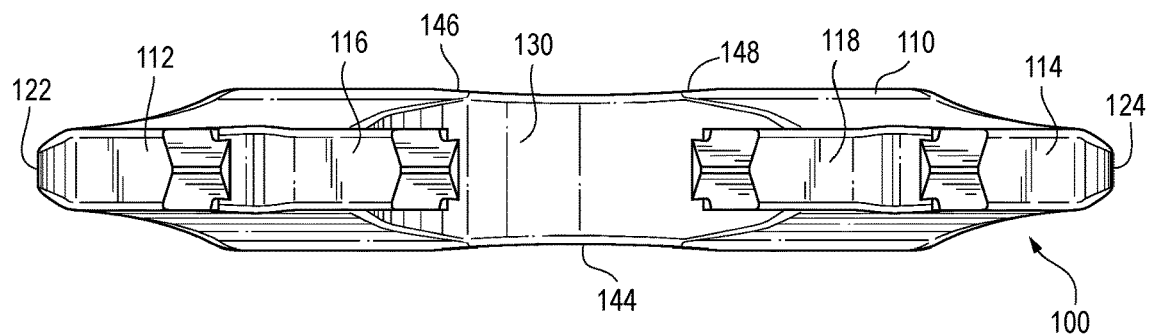
FIG. 3 is a bottom plan view of the surgical staple of FIG. 1.

Broadly, the surgical staple 100 has a bridge 110 and a plurality of legs 112, 114, 116, 118, as shown in FIGS. 1-3. The legs can number, two, three, four or any suitable number. In the illustrated examples, there are four legs, a pair of inner legs 116, 118 and a pair of outer legs 112, 114.

Figure 14:
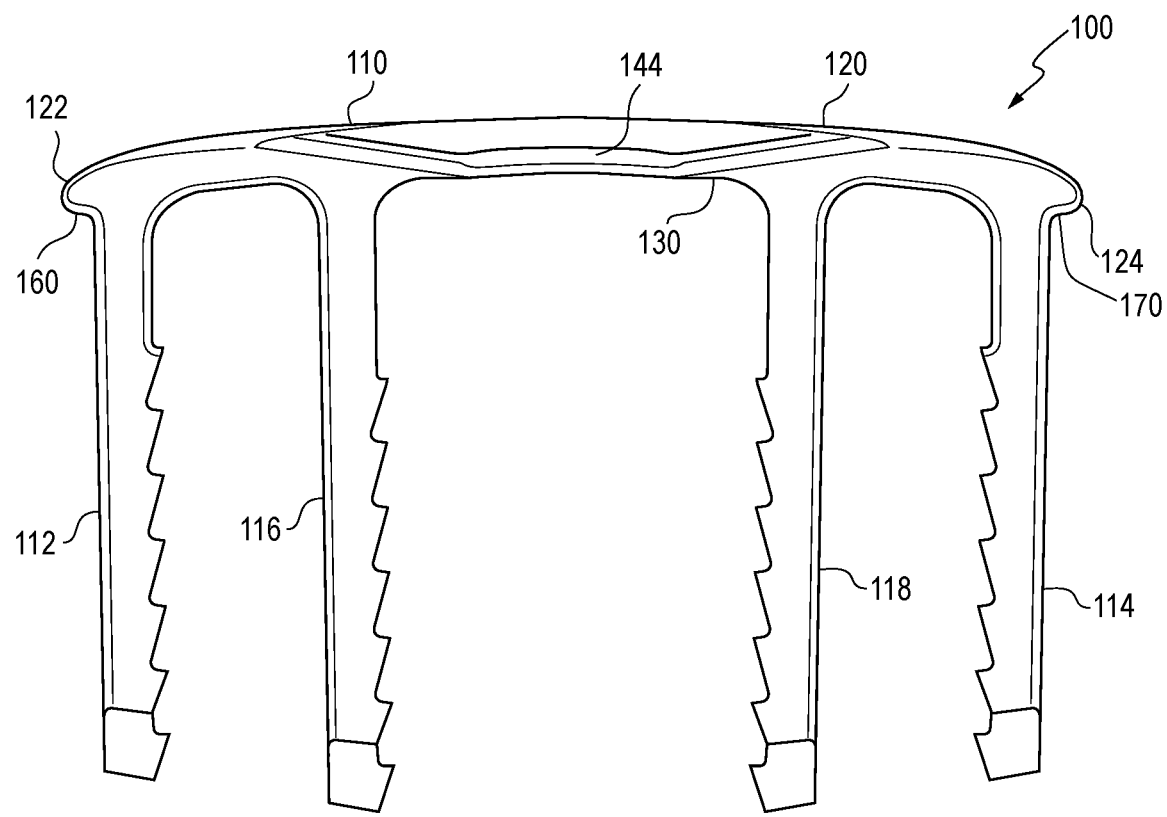
FIG. 14 is a front elevation view of the surgical staple of FIG. 1, but showing the surgical staple having been moved into a tensioned configuration as compared to the relaxed configuration shown in FIG. 1.
Figure 26:
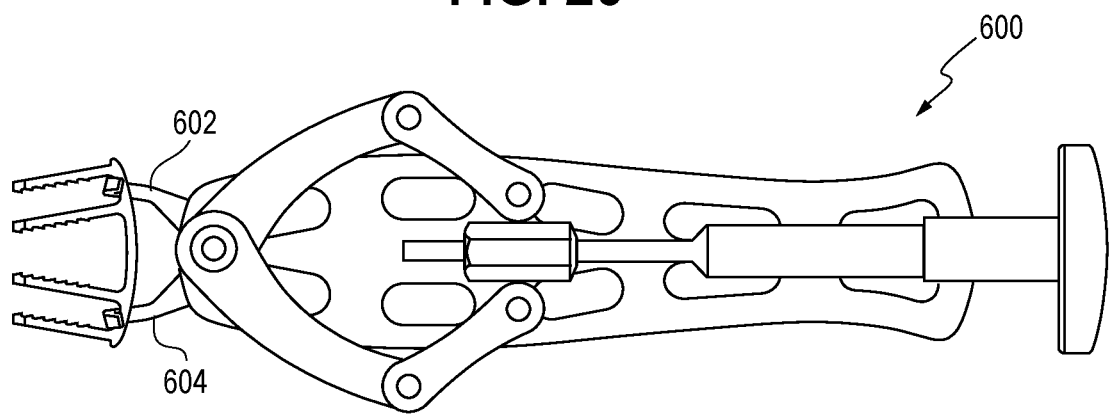
FIG. 26 is a schematic representation of a spreading tool having a first operative part and a second operative part each engaged with the surgical staple of FIG. 1 in the relaxed configuration thereof.
Figure 27:
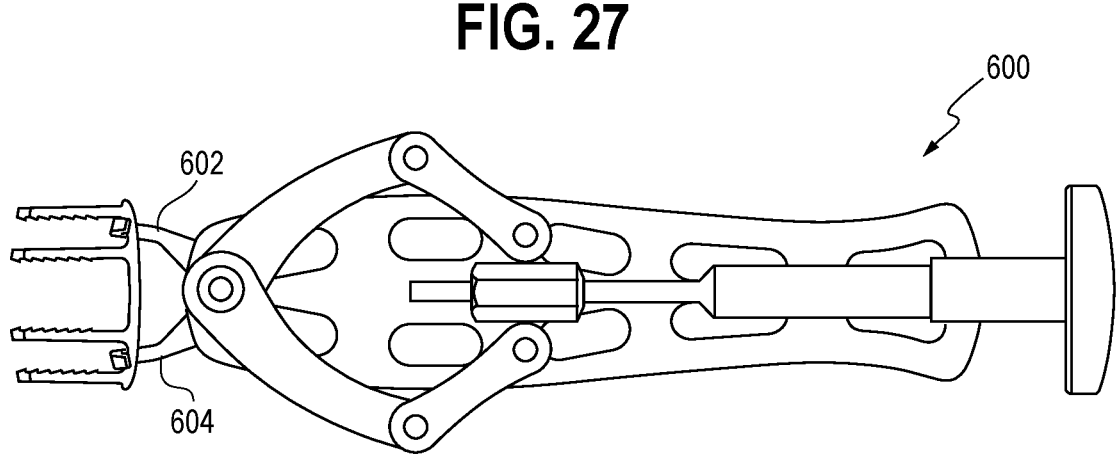
FIG. 27 is a schematic representation of the spreading tool having been used to move the surgical staple to the tensioned configuration of FIG. 14 and holding the surgical staple in the tensioned configuration.

The bridge 110 has a relaxed configuration, where the bridge 110 is arched, as shown in FIGS. 1-3, and a tensioned configuration, as shown in FIG. 14, where the bridge 110 is less arched than in the relaxed configuration. When in the relaxed configuration, the legs 112, 114, 116, 118 are in an acutely angled orientation relative to the bridge 110. As will be described further herein, the surgical staple 100 can be moved to its tensioned configuration, such as by using an insertion or spreader tool 600, such as shown in FIGS. 26 and 27, that moves and then holds the surgical staple 100 in its tensioned configuration. While in its tensioned configuration, the acuate angles between the legs 112, 114, 116, 118 and the bridge 110 are decreased as the legs 112, 114, 116, 118 are moved into a generally, though not necessarily precisely, parallel configuration relative to teach other. The legs 112, 114, 116, 118 of the surgical staple 100 can be inserted into holes drilled in a pair of adjacent bones when the surgical staple 100 is in the tensioned configuration. Once inserted or at least partially inserted, the insertion or spreader tool 600 can release to allow the surgical staple 100 to shift toward, but not necessarily into, the relaxed configuration to thereby compress the adjacent bones together. Advantageously, the shape memory properties of the staple 100 can cause the legs 112, 114, 116, 118 to want to return to their acutely angled orientation relative to the bridge 110, thereby compressing the adjacent bones together, preferably with a compressing force that is greater than if the legs 112, 114, 116, 118 in their relaxed or neutral state were generally perpendicular relative to the bridge 110.

Figure 4:
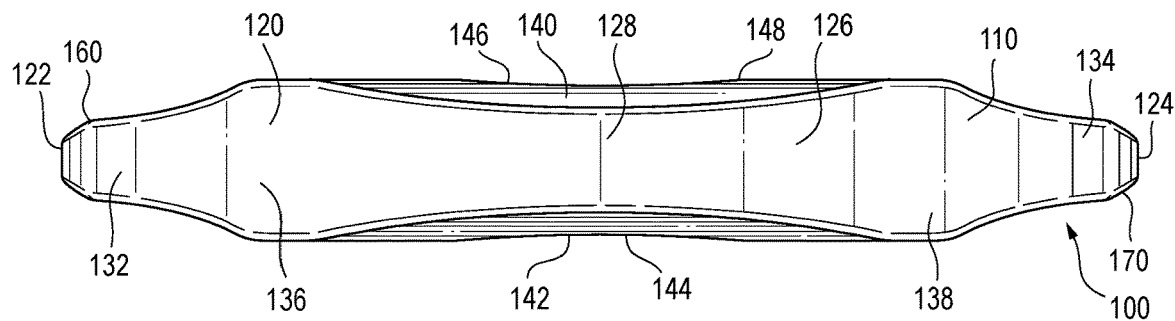
FIG. 4 is a top plan view of the surgical staple of FIG. 1.
Figure 5:
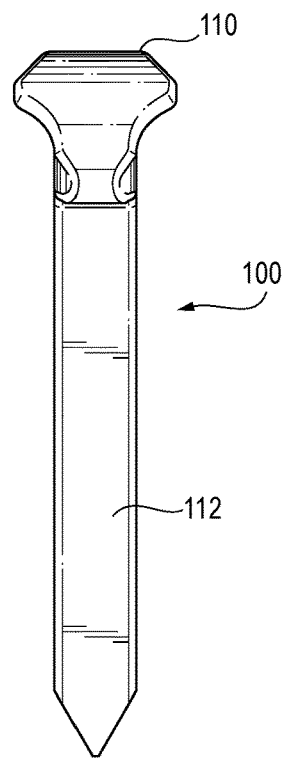
FIG. 5 is a right side elevation view of the surgical staple of the surgical staple of FIG. 1.
Figure 6:
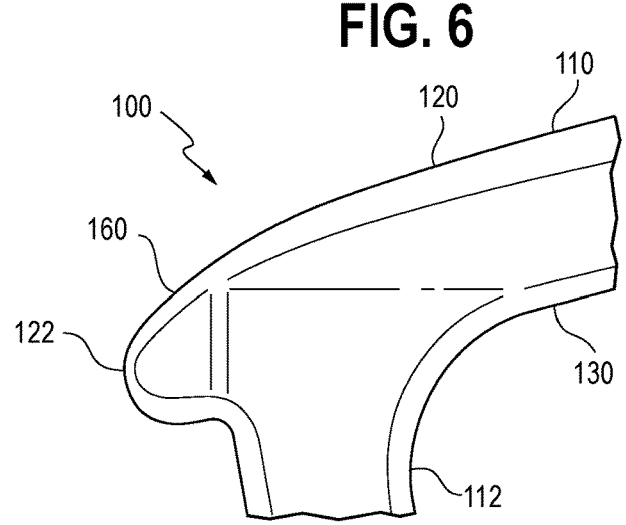
FIG. 6 is a detailed front elevation view of the first extension of surgical staple of FIG. 1 taken from region VI of FIG. 2.

The bridge 110 has an upper side 120, as shown in FIG. 4, and a lower side 130 opposite the upper side 120, as shown in FIG. 5. The bridge 110 also has a first end 122 and a second end 124. The bridge has a length extending between the first end 122 and the second end 124. The bridge 110 also has a thickness extending between the upper side 120 and the lower side 130 of the bridge 110. The dimension of the thickness varies depending upon the location along the bridge 110. At a given location along the bridge 110, the thickness is measured as the maximum thickness between the upper side 120 and the lower side 130. The bridge 110 also has a width extending perpendicular to the length and the thickness. The dimension of the width varies depending upon the location along the bridge 110. At a given location along the bridge 110, the thickness is measured as the maximum thickness of the bridge 110.

The legs 112, 114, 116, 118 depend from the lower side 130 of the bridge 110. The legs include a first leg 112 adjacent the first end 122 of the bridge 110 and a second leg 114 adjacent the second end 124 of the bridge 110. Optionally, the legs include a third leg 116 and a fourth leg 118. The third leg 116 is disposed between the first leg 112 and the fourth leg 118. The fourth leg 118 is disposed between the second leg 114 and the third leg 116. The legs 112, 114, 116, 118 each have a tip. The tip can taper to a linear intersection, as shown in FIG. 5. The legs 112, 114, 116, 118 can optionally have teeth such as those shown in FIGS. 1 and 2.

Figure 28:
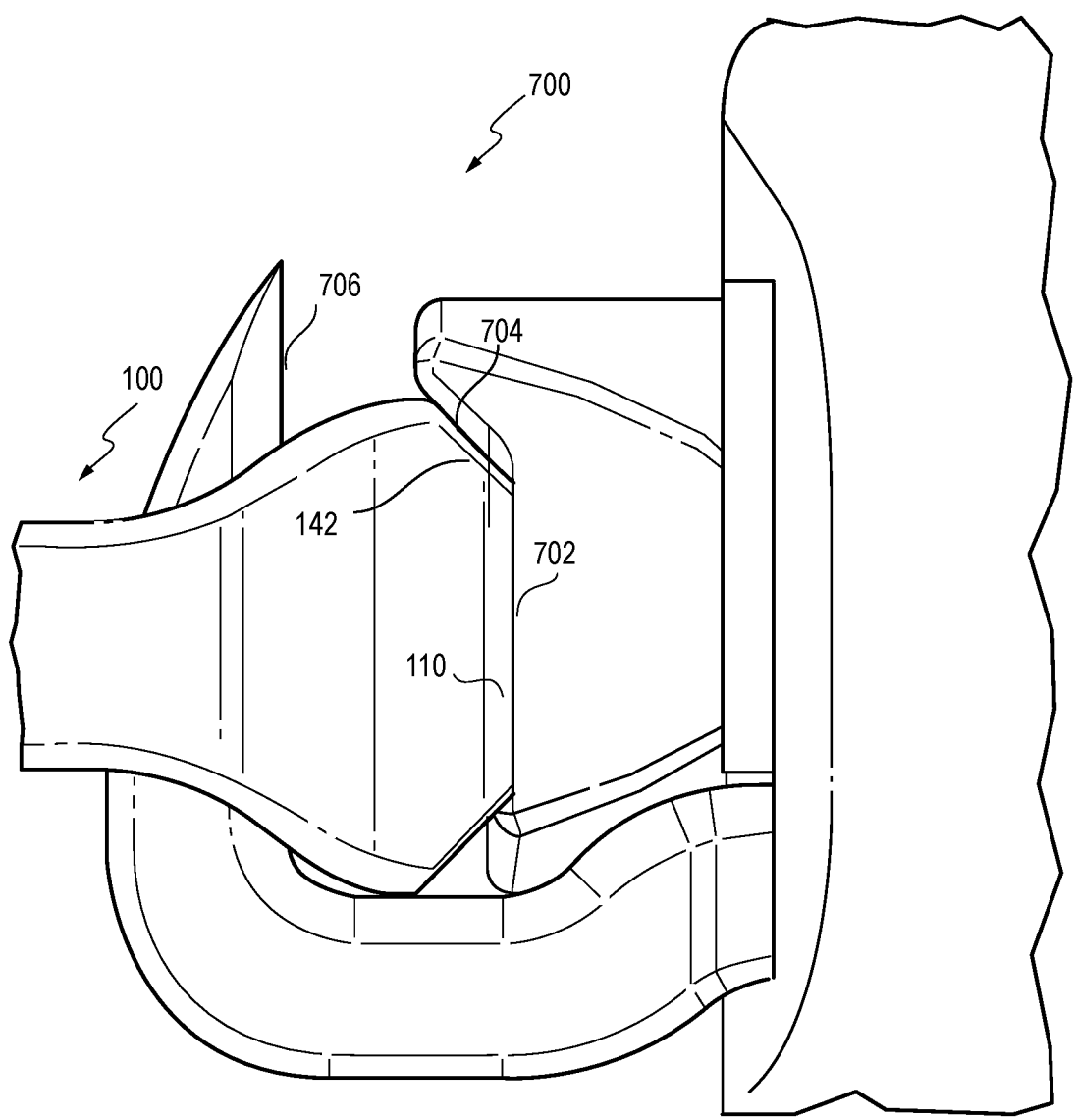
FIG. 28 is a schematic representation of an operating end of a spreading tool, showing surfaces of the surgical staple interfacing with a nipple on a compression rod of the tool.

Turning to further details of the bridge 110, the upper side 120 of the bridge can have a curved surface 126 extending from the first end 122 to the second end 124 of the bridge 110, as shown in FIG. 4. Preferably the curved surface 126 is smooth, such as that it lacks protuberances and/or recesses. The lack of protuberances and recesses can potentially reduce irritation of adjacent tissue or the like when the surgical staple 100 is implanted. However, the curved surface 126 does not have to be smooth. The curved surface 126 has a narrowed middle region 128, a first narrowed region 132 adjacent the first end 122 and a second narrowed region 134 adjacent the second end 124. The curved surface 126 includes a first wider region 136 between the first narrowed region 132 and the narrowed middle region 128. The curved surface 126 also includes a second wider region 138 between the second narrowed region 134 and the narrowed middle region 128. Preferably the curved surface 126 is symmetric about the middle thereof in both a direction corresponding to the length of the bridge 110 and a direction corresponding to the width of the bridge 110. However, such symmetry is not required. The narrowed middle region 128 is narrower in a direction corresponding to the width of the bridge 110 as compared to both the first wider region 136 and the second wider region 138. The first narrowed region 132 and the second narrowed region 134 are each narrower in a direction corresponding to the width of the bridge 110 as compared to both the first wider region 136 and the second wider region 138. The upper side 120 of the bridge 110 includes a pair of lateral scallops, tapered or inclined surfaces 140, 142 on each side of the narrowed middle region 128 of the curved surface 126. The surfaces 140, 142 can allow for the surrounding soft tissue, in use, to fall away from the top of the bridge without any sharp edges or points that could lead to irritation and/or dehiscence. The surfaces 140, 142 can also beneficially provide for an interface with a staple inserter tool 700, such as the tool disclosed U.S. patent application Ser. No. 18/131,141, filed Apr. 5, 2023, which is hereby incorporated by reference in its entirety. More specifically, the surfaces 140, 142 of the bridge 110 of the surgical staple 100 can interface with at least one matching inclined surface 702 of the seat 704 on a compression rod or shaft of the tool 700 to restrict the staple from slipping out during expansion and insertion. The angled faces of the surfaces 140, 142 provide more surface area for the seat 704 to engage with when pulled toward the seat 704 by one or more jaws 706, thereby helping to keep the staple 100 firmly seated, as shown in FIG. 28.

The width of the bridge 110 has a waisted or reduced width portion 144 adjacent to the narrowed middle region 128 of the curved surface 126 as compared to a pair of larger width portions 146 148 disposed on opposite sides of the reduced width portion 144, as shown in FIGS. 3, 4, 9 and 10. Preferably the reduced width portion 144 is centered on the length of the bridge 110.

The reduced width portion 144 of the bridge 110 can advantageously allow for the bridge of the surgical staple 100 to be more likely to bend at the reduced width portion 144 of the width of the bridge 110. This can be particularly advantageous when the surgical staple 100 has four legs 112, 114, 116, 118. That is because allowing for the bridge 110 of the surgical staple 100 to be more likely to bend at the reduced width portion 144 of the width of the bridge 110 as opposed to i) between the first leg 112 and the third leg 116; and i) between the second leg 114 and the fourth leg 118 when the surgical staple 100 is moved from the relaxed configuration to the tensioned configuration can reduce relative movement between the first and third legs 112, 116 and between the second and fourth legs 114, 118 to facilitate insertion into predrilled holes in the adjacent bones.

Another advantage of the reduced width portion 144 of the width of the bridge 110 is that it can provide for a visual target for centering the surgical staple 100 during insertion, such as improved fluoroscopic visibility. The reduced width portion 144 of the width of the bridge 100 can also function as an identifying feature allowing for ease of identification under x-ray, for example.

Yet another advantage of the reduced width portion 144 of the width of the bridge 110 is that centering of the surgical staple 100 relative to the spreader tool 600 can be improved by providing a structural feature for such centering.

Figure 13:
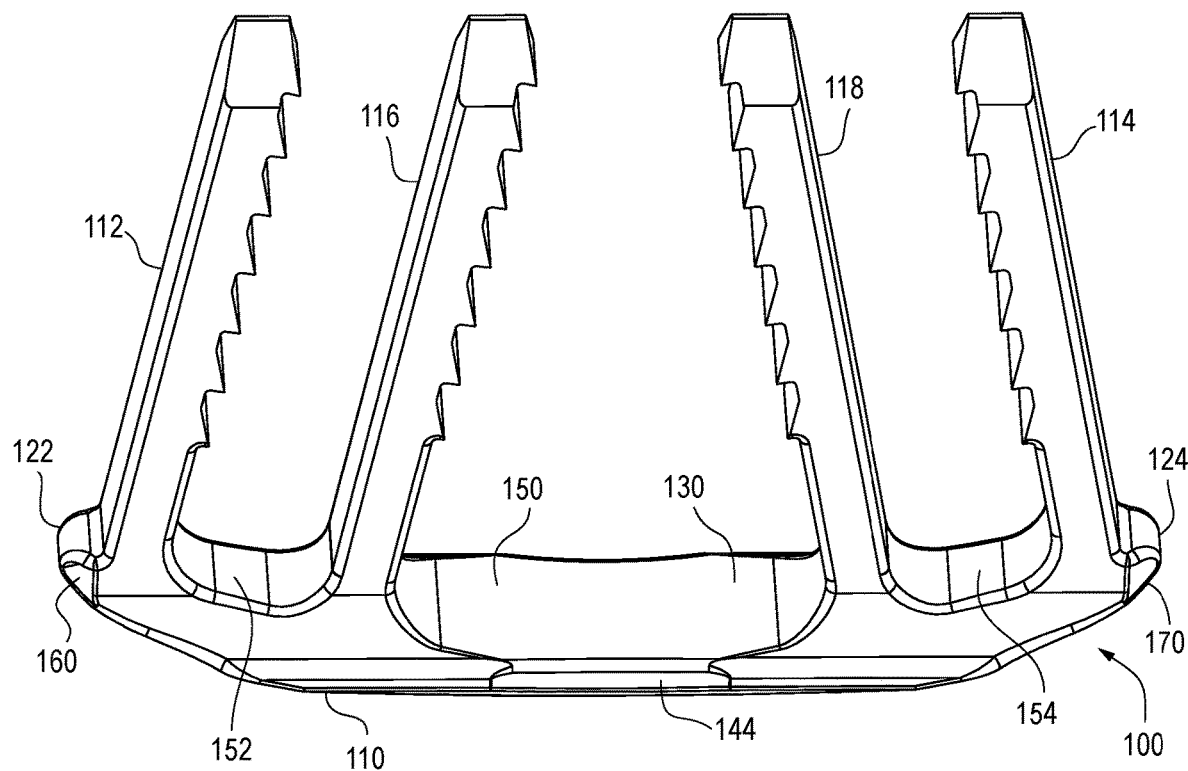
FIG. 13 is a bottom perspective view of the surgical staple of FIG. 1.

The lower side 130 of the bridge 110 of the surgical staple 100, shown in FIGS. 3 and 13, has an intermediate smooth surface 150 extending between the third and fourth legs 116, 118, a first smooth surface 152 extending between the first and third legs 112, 116 and a second smooth surface 154 extending between the second and fourth legs 114, 118. Preferably, the first smooth surface 152 and the second smooth surface 154 each have a maximum width less than a maximum width of the intermediate smooth surface 150. This mirrors the narrowing of the upper side of the bridge 110 as well. These outer legs 112, 114 are not contributing nearly as much to the compressive property of the staple 100 as compared to the inner legs 116, 118, and thus do not need as wide of a bridge 110 at their intersection with the bridge 110 to support their function. The outer legs 112, 114 instead contribute more to rotational stability beyond what a two-legged staple can provide. Furthermore, the narrowed upper and lower bridge portion in these sections can contribute to less soft tissue irritation and may allow for a small incision to be made in order to place the staple.

Figure 7:
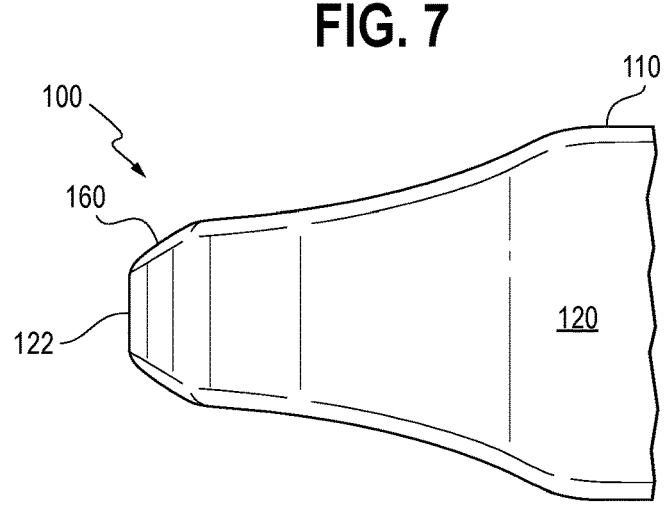
FIG. 7 is a detailed top plan view of the first extension of surgical staple of FIG. 1 taken from region VII of FIG. 4.
Figure 8:
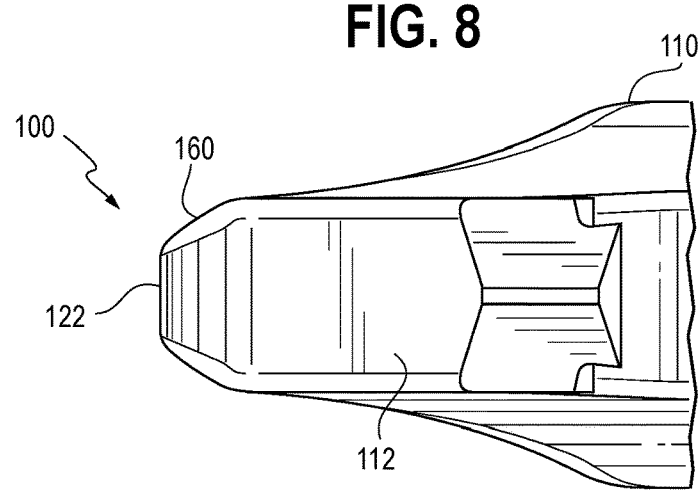
FIG. 8 is a detailed bottom elevation view of the first extension of surgical staple of FIG. 1 taken from region VIII of FIG. 3.
Figure 9:
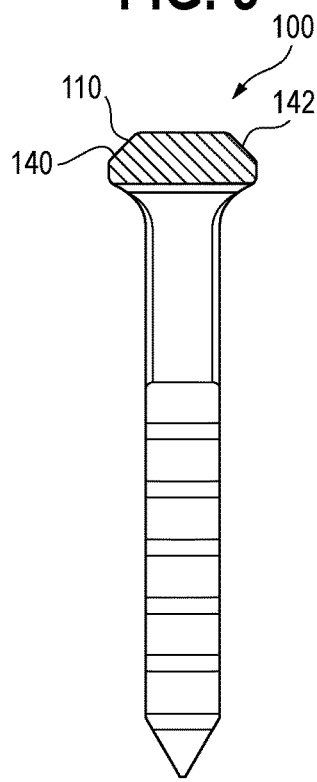
FIG. 9 is a cross-sectional view of the surgical staple of FIG. 1, taken along line IX-IX of FIG. 2.
Figure 10:
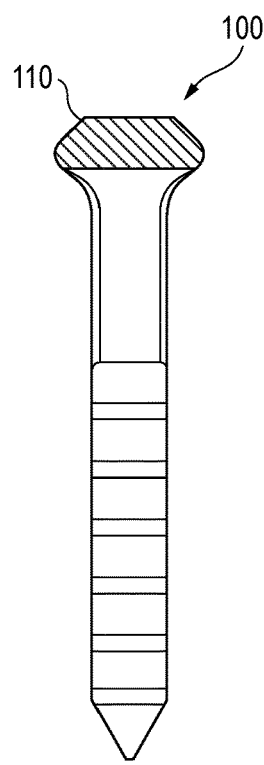
FIG. 10 is a cross-sectional view of the surgical staple of FIG. 1, taken along line X-X of FIG. 2.
Figure 11:
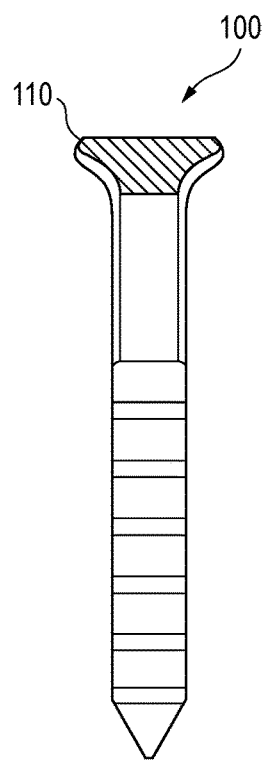
FIG. 11 is a cross-sectional view of the surgical staple of FIG. 1, taken along line XI-XI of FIG. 2.
Figure 12:
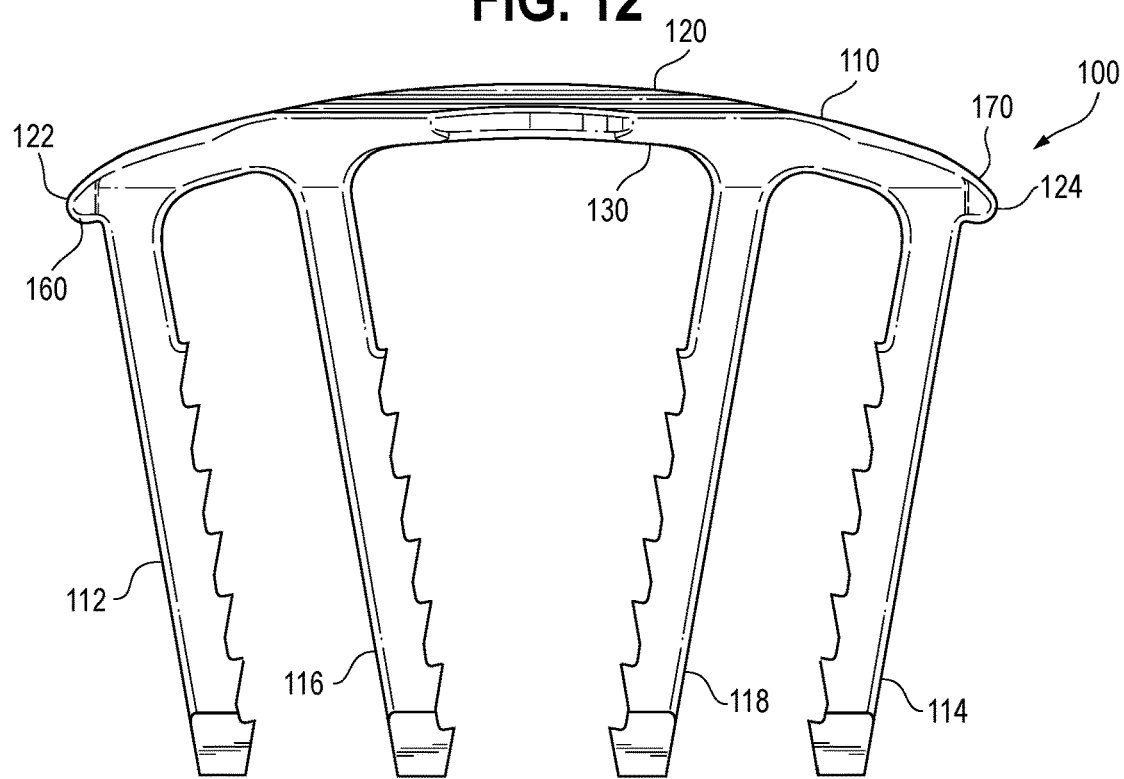
FIG. 12 is a cross-sectional view of the surgical staple of FIG. 1, taken along line XII-XII of FIG. 4.

The bridge 110 has a first extension 160 adjacent the first end 122 of the bridge 110 and extending on an opposite side of the first leg 112 relative to the second leg 114. The bridge 110 also has a second extension 170 adjacent the second end 124 of the bridge 110 and extending on an opposite side of the second leg 114 relative to the first leg 112. The first extension 160 has a tapering thickness decreasing toward the first end 122 of the bridge 110, as shown in detail in FIG. 6. Likewise, the second extension 170 has a tapering thickness decreasing toward the second end 124 of the bridge 110. The tapering thicknesses of the first extension 160 and the second extension 170 is predominately in the upper side 120 as opposed to the lower side 130 of the bridge 110. The first end 122 of bridge 110 and the second end 124 of the bridge 110 are each rounded such that the thickness is decreasing at the first end 122 of the bridge 110, as shown in detail in FIG. 6, and second end 124 of the bridge 110. Furthermore, the first extension 160 can taper in the width direction such that the width decreases in a direction extending toward the first end 122, as shown in FIGS. 7 and 8. Likewise, the second extension 170 can taper in the width direction such that the width decreases in a direction extending toward the second end 124.

The geometries of the first extension 160 and the second extension 170 can provide several advantages when the surgical staple 100 is implanted in adjacent bones. First, the first extension 160 and the second extension 170 can advantageously reduce rocking of the surgical staple 100 when implanted. Specifically, rocking in a direction along the length of the bridge 110 can be reduced. The reduction in rocking can further be enhanced when the portions of the bottom surface 130 of the bridge 110 that coincide with the first extension 160 and the second extension 170 are dimensioned to abut a bone or other surface when implanted, such as shown for example in FIG. 17. This can aid in prevention of plantar gapping in dorsiflexion due to the bottoms of the first extension 160 and the second extension 170 sitting on or abutting the bone. Second, such abutment can advantageously reduce irrigation by blocking tissue and other matter from becoming disposed between the bone and the surgical staple 100. Soft tissue irritation can be reduced when the bottoms of the first extension 160 and the second extension 170 sit on or abut the bone. Third, the tapering of the first extension 160 and the second extension 170 in the thickness direction, and predominately in the upper side 120 as compared to the lower side 130 of the bridge 110, can advantageously reduce the first and second ends 122, 124 from protruding when implanted. Fourth, the tapering of the first extension 160 and the second extension 170 in the width direction can advantageously reduce the first and second ends 122, 124 from protruding when implanted. Fifth, the rounded first end 122 of the bridge 110 and the rounded second end 124 of the bridge 110 can also advantageously reduce the first and second ends 122, 124 from protruding when implanted. The tapering and/or rounding can also reduce soft tissue irritation because the tissue can more easily slide over such geometries. Any one, combination of some or combination of all of the these geometries of the first extension 160 and the second extension 170 can be present in the surgical staple 100. Having the first extension 160 and the second extension 170, as compared to having no extension, can allow for the thickness and/or width at the intersections of the legs 112, 114, 116, 118 and the bridge 110 to be larger as compared to if such geometries were incorporated into a surgical staple having no such extensions. This can advantageously reduce potential stress concentrations and breaking of the legs from the bridge at the intersections thereof.

Although a first extension 160 and a second extension 170 are discussed and shown in the figures, a surgical staple may optionally incorporate only of the extensions.

In the embodiment of FIGS. 1-17, the tips of each of the legs 112, 114, 116, 118 terminate at a common distal extent from the bridge 110 when in the relaxed configuration. When in the tensioned configuration, shown in FIG. 14, the tips of the first and second legs 112, 114 each terminate at a different distal extent as compared to the tips of the third and fourth legs 116, 118. However, other leg lengths can also be used as may be suitable for a given surgical procedure. For example, the use of a staple with two legs shorter than another two legs can beneficially be used for various procedures, such as when one of the bones or the operative portion of the bone has a thickness that may not warrant or be suitable for a longer leg. In the first alternative surgical staple 200, shown in FIGS. 18 and 19, each of legs terminates at a different distal extend from the bridge. In the third alternative surgical staple 400, shown in FIGS. 22 and 23, the first leg and the third leg terminate at a common distal extent from the bridge, but the fourth leg and the second leg each terminate at different distal extents different from both each other and the first leg and the third leg.

The spacing between the legs of the surgical staple can also be varied. For example, in the second alternative surgical staple 300, shown in FIGS. 20 and 21, the length of the bridge is less than that of FIGS. 1-17. Also by way of example, in the fourth alternative surgical staple 500, shown in FIGS. 24 and 25, the length of the bridge is less than that of FIGS. 18 and 19.

The first, second, third and fourth alternative surgical staples 200, 300, 400, 500 are similar in construction to that of FIGS. 1-17, but for the differences in the legs and bridge length discussed above.

Figure 15:
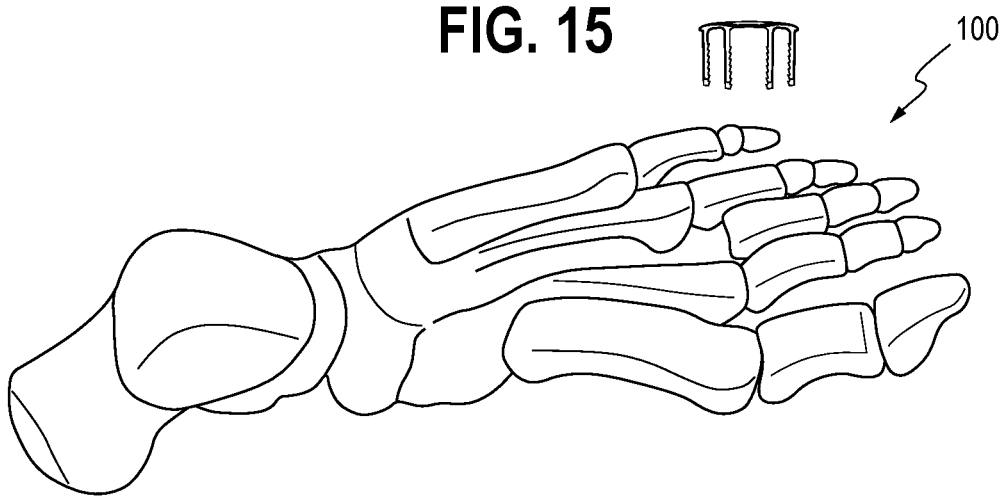
FIG. 15 is a schematic view of bones of a foot, showing drilled holes for receiving the surgical staple of FIG. 1, shown in the tensioned configuration thereof.
Figure 16:
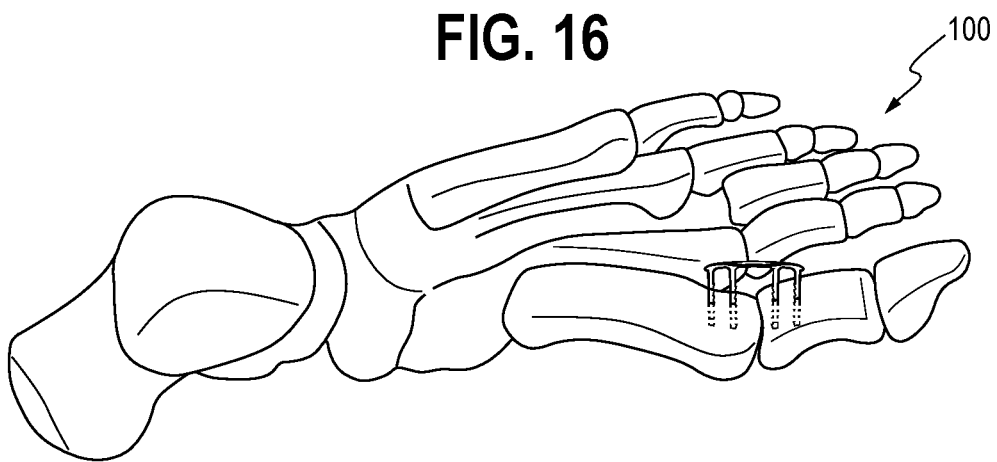
FIG. 16 is a schematic view similar to that of FIG. 12, but showing the surgical staple of FIG. 1 having been inserted into the drilled holes and allowed to return toward the relaxed configuration to compress adjacent bones together.
Figure 17:
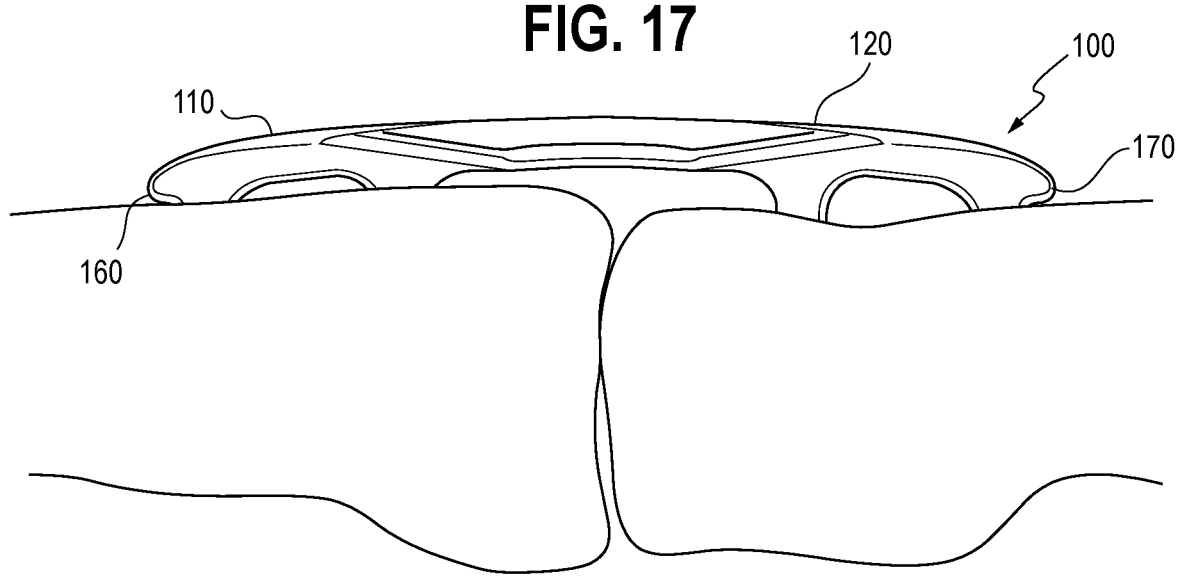
FIG. 17 is a detailed schematic view similar to that of FIG. 13, and showing a first extension of the bridge and a second extension of the bridge each abutting an underlying bone.
Figure 18:
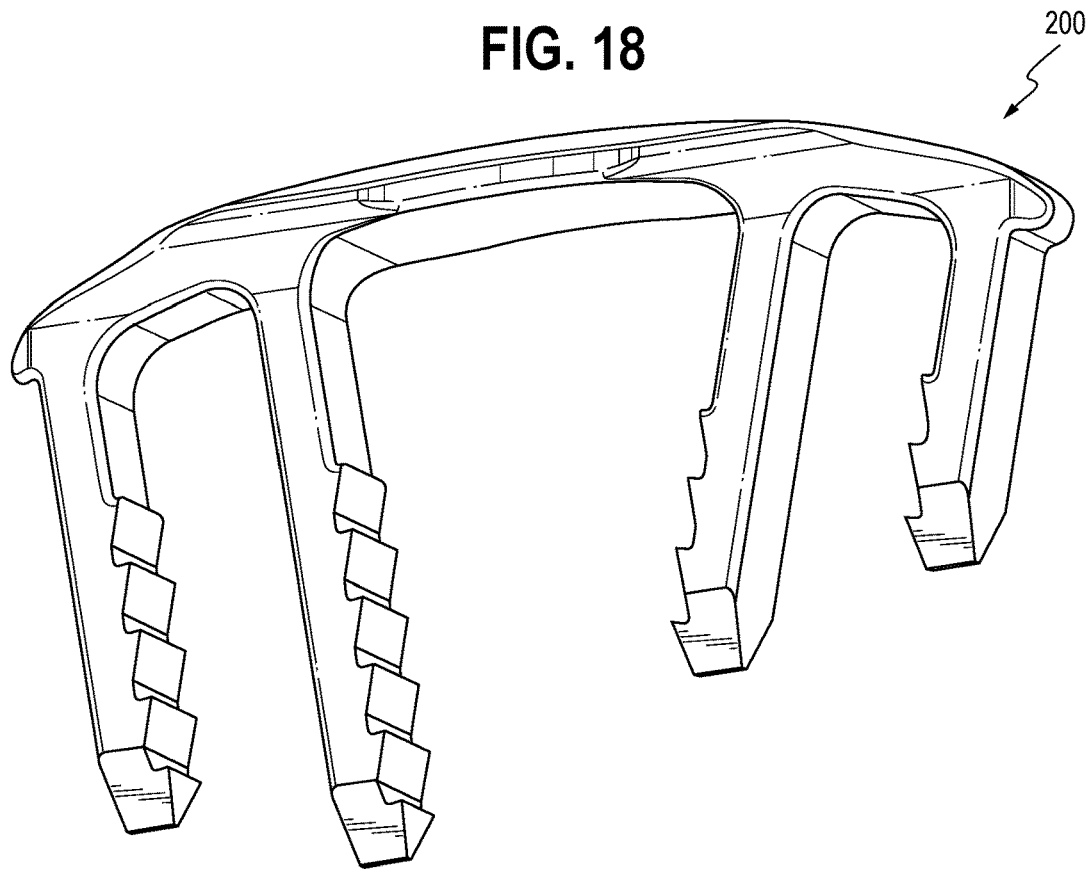
FIG. 18 is a perspective view of a first alternative surgical staple, the first alternative surgical staple having four legs each with a tip of different lengths.
Figure 19:
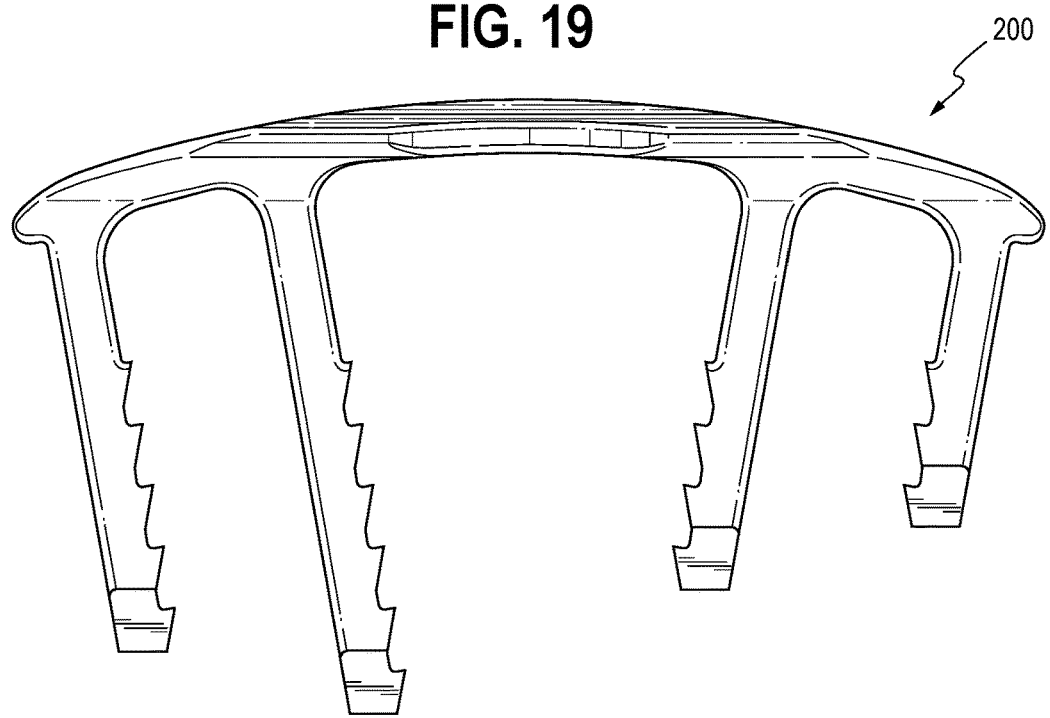
FIG. 19 is a front elevation view of the first alternative surgical staple of FIG. 18.
Figure 20:
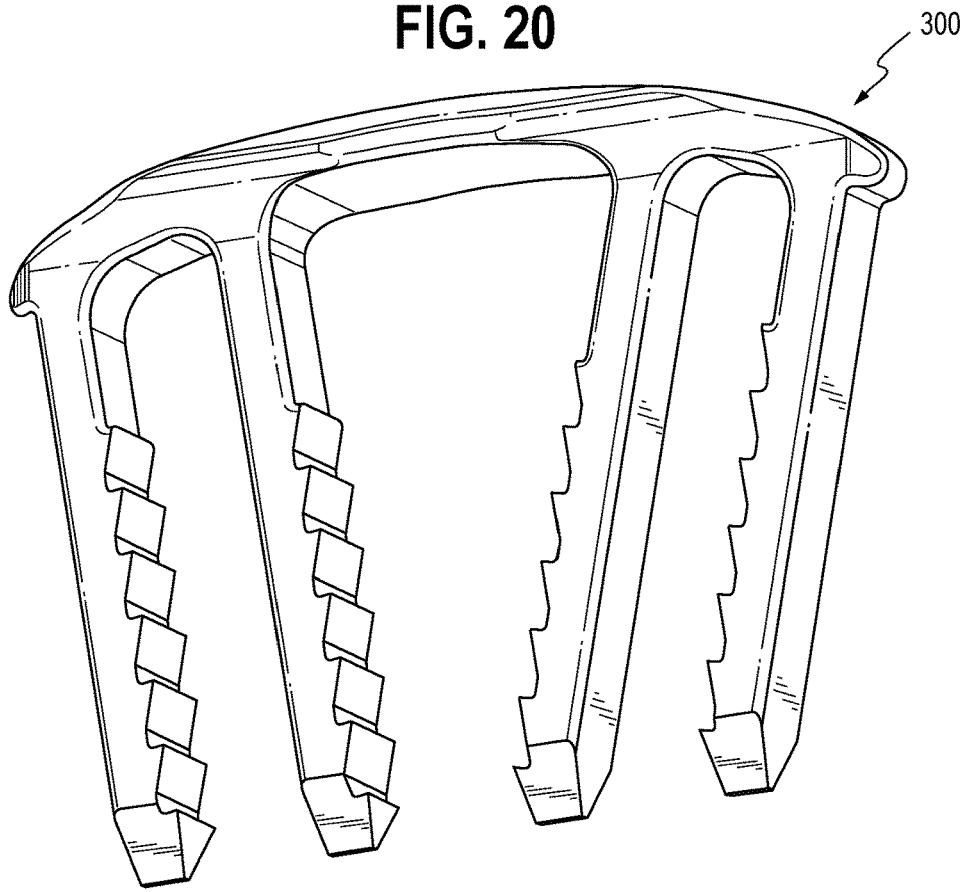
FIG. 20 is a perspective view of a second alternative surgical staple, the second alternative surgical staple having four legs each of the same length.
Figure 21:
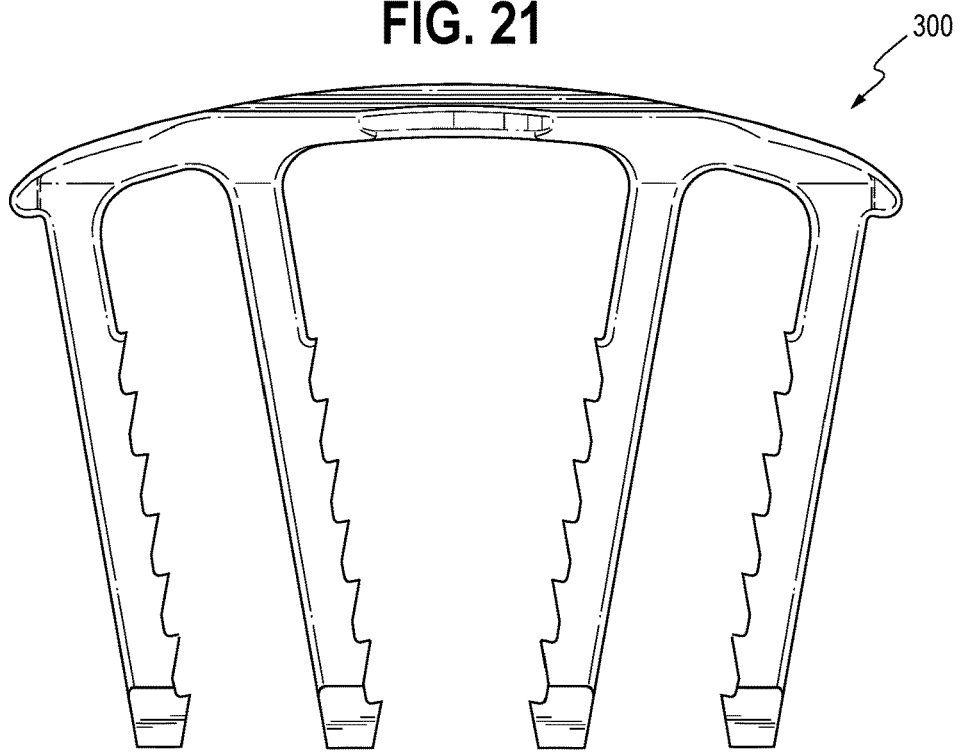
FIG. 21 is a front elevation view of the second alternative surgical staple of FIG. 20.
Figure 22:
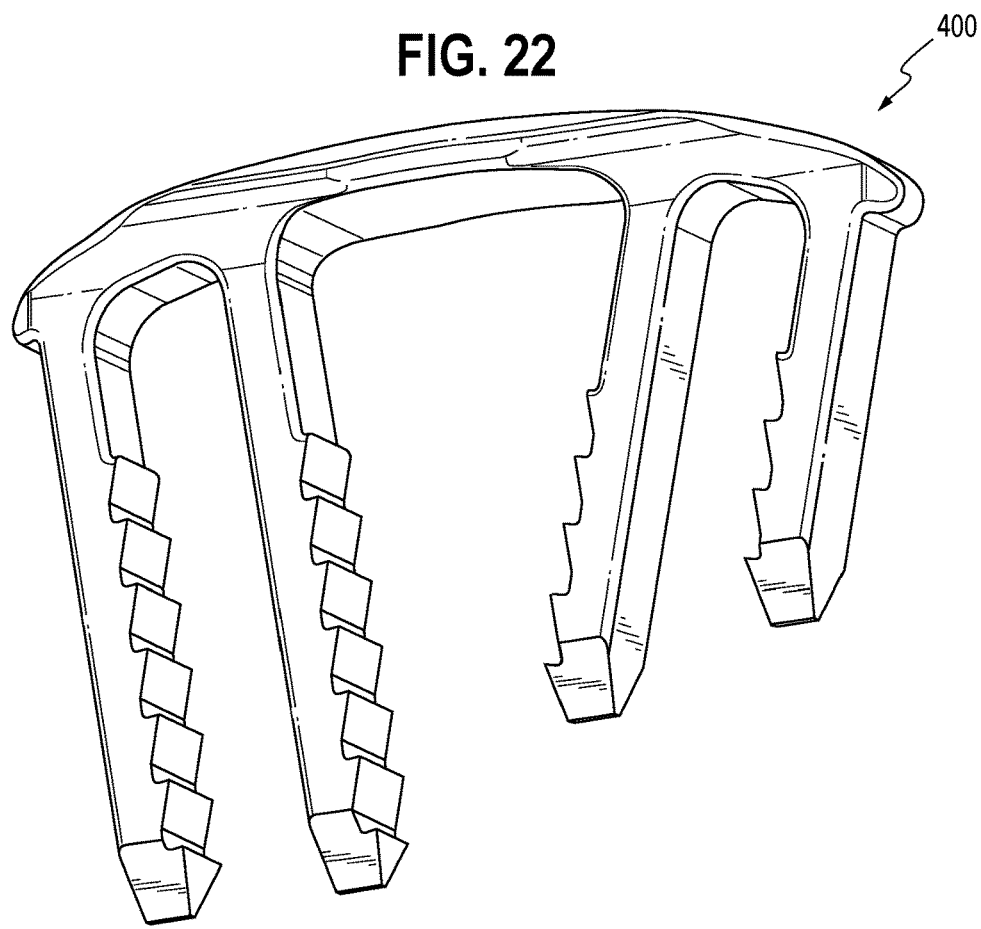
FIG. 22 is a perspective view of a third alternative surgical staple, the third alternative surgical staple having two legs each of the same length and two legs of differing lengths.
Figure 23:
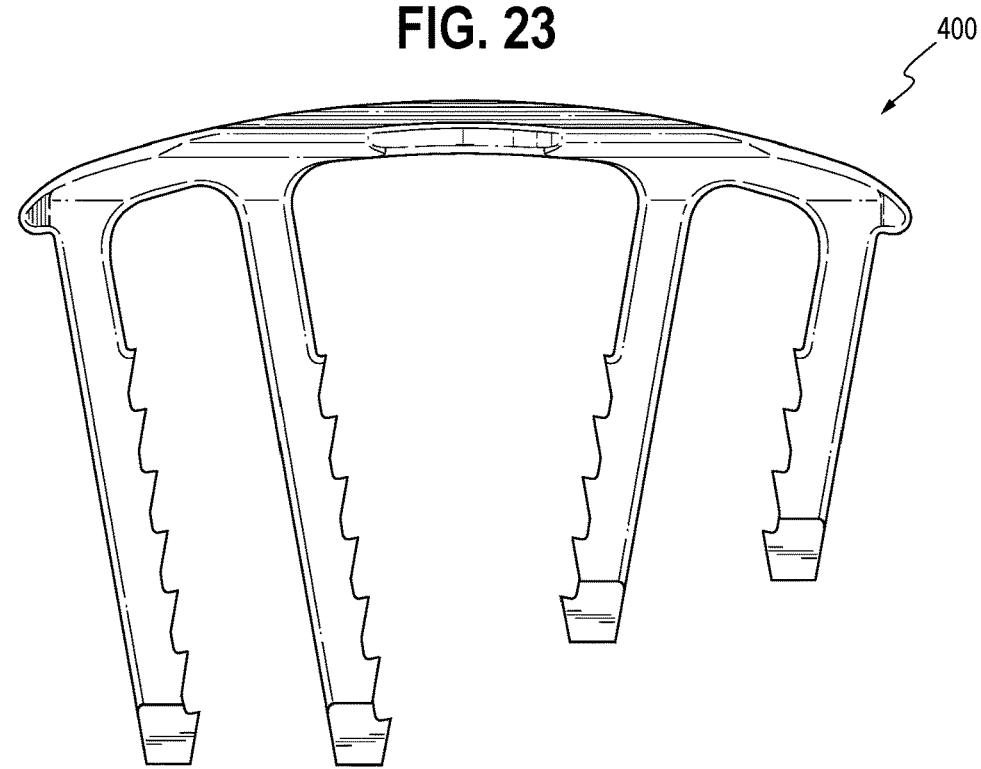
FIG. 23 is a front elevation view of the third alternative surgical staple of FIG. 22.
Figure 24:
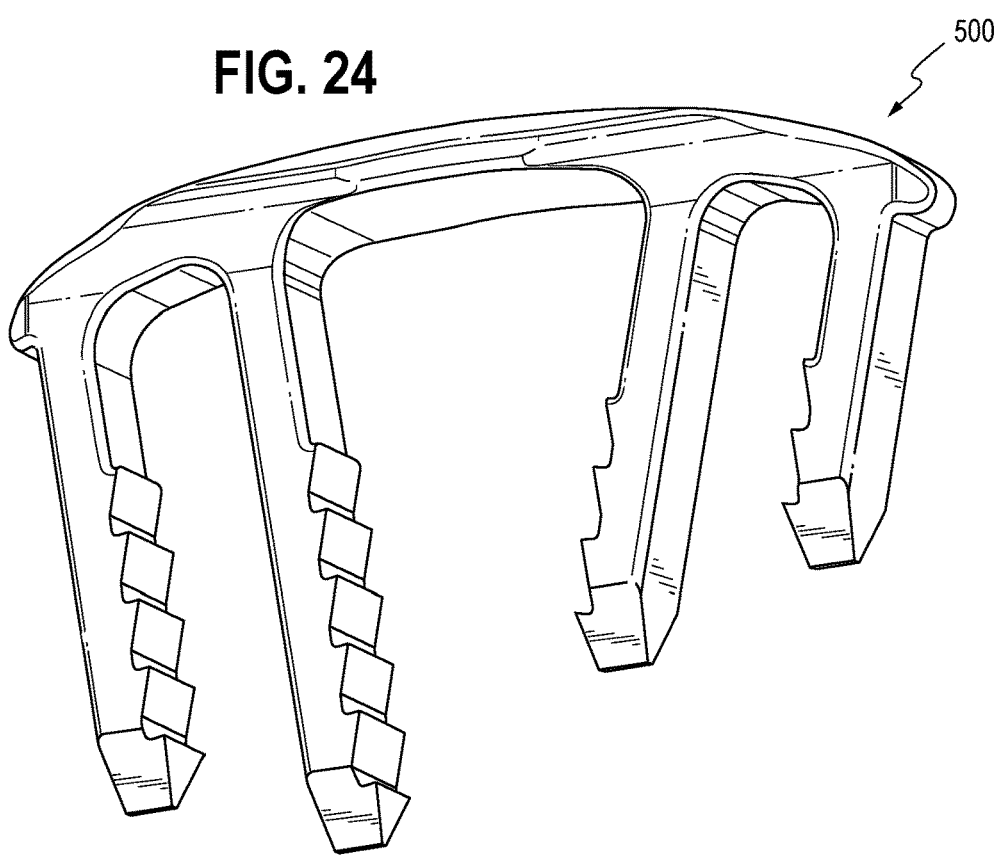
FIG. 24 is a perspective view of a fourth alternative surgical staple, the fourth alternative surgical staple having four legs each of different lengths.
Figure 25:
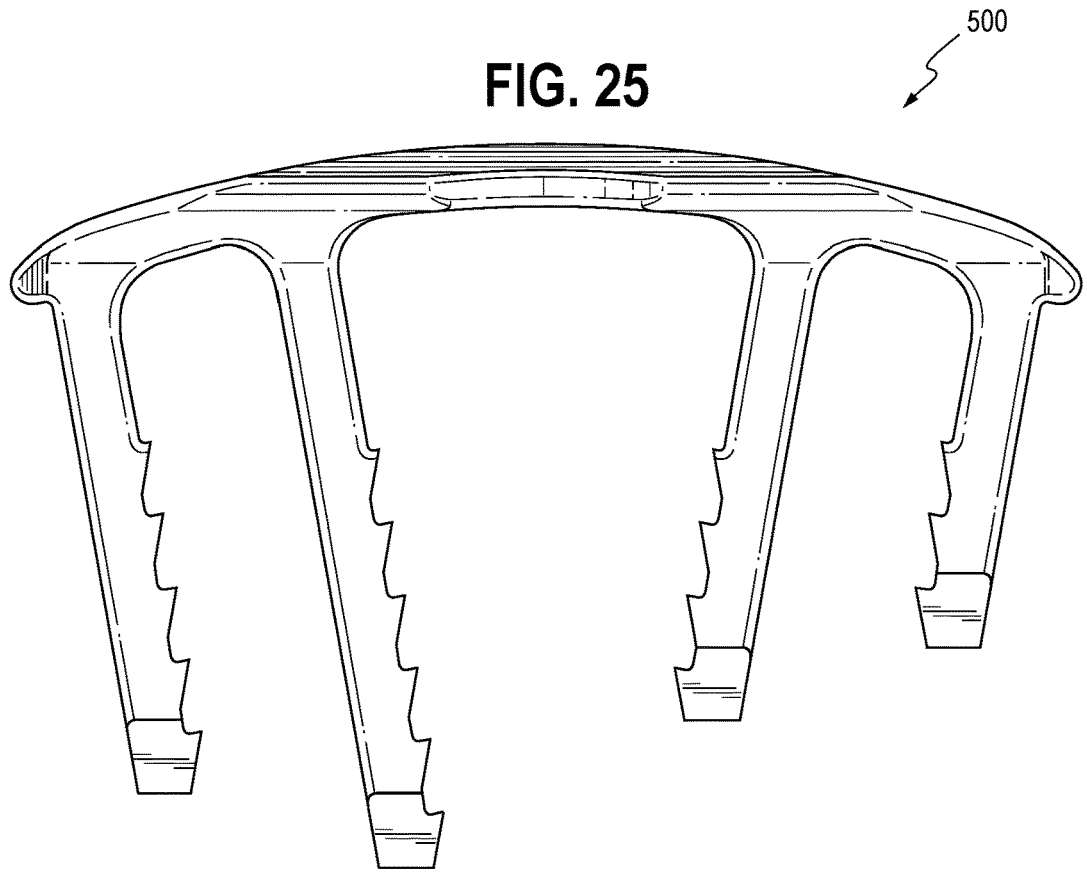
FIG. 25 is a front elevation view of the fourth alternative surgical staple of FIG. 24.

Turning now to a method of implanting the surgical staple 100 into one or more bones or bone pieces, the method can include drilling holes in the one or more bones or bone pieces for receiving the legs 112, 114, 116, 118 of the surgical staple 100, such as shown in FIG. 15. The method can also include moving the surgical staple 100 from the relaxed configuration, shown in FIG. 2, to the tensioned configuration, shown in FIG. 14. The method can further include inserting the legs 112, 114, 116, 118 of the surgical staple 100 into the holes while the surgical staple 100 is in the tensioned configuration, as shown in FIG. 16. Once the legs 112, 114, 116, 118 have been inserted to the holes, the method can include allowing the surgical staple 100 to move from the tensioned configuration toward the relaxed configuration and into an installed configuration whereby the surgical staple 100 compresses the one or more bones or bone pieces together.

An insertion tool 600, such as that disclosed in U.S. patent application Ser. No. 17/322,580, filed May 17, 2021, published as U.S. Pat. Appl. Publ. No. 2022/0361877, which is hereby incorporated herein by reference in its entirety, can engage with the surgical staple 100 to bend and temporarily hold the surgical staple 100 in the tensioned configuration for insertion into the holes. Once the legs 112, 114, 116, 118 are almost completely inserted, the insertion tool 600 can be disengaged from the surgical staple 100 and the legs 112, 114, 116, 118 inserted the rest of the way into the holes. As described above, the shape memory properties of the surgical staple 100 can cause the legs 112, 114, 116, 118 to want to return to their acutely angled orientation relative to the bridge 110, thereby compressing the adjacent bones together, preferably with a compressing force that is greater than if the legs 112, 114, 116, 118 in their relaxed or neutral state were generally perpendicular relative to the bridge 110. Preferably, though not necessarily, in the installed configuration, the lower side 130 of the bridge 110 at the first and second extensions 160, 170 is abutting the one or more bones or bone pieces.

During moving the surgical staple 100 from the relaxed configuration to the tensioned configuration, the bridge 110 is bent to a greater amount at the reduced width portion 144 of the width of the bridge 110 as opposed to i) between the first leg 112 and the third leg 116; and i) between the second leg 114 and the fourth leg 118.

The moving of the surgical staple 100 from the relaxed configuration to the tensioned configuration can include contacting a side of the third leg 116 facing the fourth leg 118 with a first operative part 602 of a spreading tool, such as one of the jaws of the inserter 600, and contacting a side of the fourth leg 118 facing the third leg 116 with a second operative part 602 of the spreading tool, such as another of the jaws of the inserter 600, as shown in FIG. 26. When the first operative part 602 of the spreading tool 600 and the second operative part 604 of the spreading tool 600 are moved away from each other, as shown in FIGS. 26 and 27, the surgical staple 100 can be moved from the relaxed configuration to the tensioned configuration. Conversely, when the first operative part 602 of the spreading tool 600 and the second operative part 604 of the spreading tool 600 are moved toward each other, the surgical staple 100 can return toward, but not necessarily to, the relaxed configuration when implanted.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims.

The invention claimed is:

1. A surgical staple comprising:
a bridge having an upper side, a lower side opposite the upper side, a first end and a second end; and
a plurality of legs depending from the lower side of the bridge, including at least a first leg adjacent the first end of the bridge and a second leg adjacent the second end of the bridge, the legs each having tips at opposite ends of the legs relative to the bridge;
the bridge further having:
a length extending between the first end and the second end, a thickness extending between the upper side and lower side of the bridge and a width extending perpendicular to the length and the thickness,
the upper side having a smooth curved surface extending from the first end to the second end of the bridge, the smooth curved surface having a narrowed middle region, a first narrowed region adjacent the first end and a second narrowed region adjacent the second end,
the width including a reduced width portion adjacent the narrowed middle region of the smooth curved surface as compared to a pair of larger width portions disposed on opposite sides of the reduced width portion, and
a first extension of the bridge adjacent the first end of the bridge and extending on an opposite side of the first leg relative to the second leg, a second extension of the bridge adjacent the second end of the bridge and extending on an opposite side of the second leg relative to the first leg, the first extension having a tapering thickness decreasing toward the first end and the second extension having a tapering thickness decreasing toward the second end, the tapering thicknesses being predominately in the upper side as opposed to the lower side of the bridge;
wherein the surgical staple has a relaxed configuration, where the bridge is arched, and a tensioned configuration, whereby the bridge is less arched than in the relaxed configuration and the tips of at least two of the legs are further apart as compared to in the relaxed configuration, the surgical staple being biased into the relaxed configuration.

2. The surgical staple of claim 1, wherein the plurality of legs includes a third leg and a fourth leg, the third leg being disposed between the first leg and the fourth leg, and the fourth leg being disposed between the second leg and the third leg.

3. The surgical staple of claim 2, wherein at least two of the first leg, second leg, third leg and fourth leg terminate at a common distal extent from the bridge.

4. The surgical staple of claim 2, wherein at least two of the first leg, second leg, third leg and fourth leg terminate at different distal extents from the bridge.

5. The surgical staple of claim 2, wherein the first, second, third and fourth legs terminate at a common distal extent from the bridge.

6. The surgical staple of claim 2, wherein the reduced width portion of the width of the bridge is disposed between the third and fourth legs.

7. The surgical staple of claim 6, wherein the bridge of the surgical staple is more likely to bend at the reduced width portion of the width of the bridge as opposed to i) between the first leg and the third leg; and i) between the second leg and the fourth leg when the surgical staple is moved from the relaxed configuration to the tensioned configuration.

8. The surgical staple of claim 2, wherein the upper side of the bridge includes a pair of lateral inclined surfaces on each side of the narrowed middle region of the smooth curved surface.

9. The surgical staple of claim 2, wherein the lower side of the bridge of the surgical staple has an intermediate smooth surface extending between the third and fourth legs, a first smooth surface extending between the first and third legs and a second smooth surface extending between the second and fourth legs, the first smooth surface and the second smooth surface each having a maximum width less than a maximum width of the intermediate smooth surface.

10. A method of implanting the surgical staple of claim 2 into one or more bones or bone pieces, the method comprising:
drilling holes in the one or more bones or bone pieces for receiving the legs of the surgical staple;

moving the surgical staple from the relaxed configuration to the tensioned configuration;

inserting the legs of the surgical staple into the holes while the surgical staple is in the tensioned configuration; and allowing the surgical staple to move from the tensioned configuration toward the relaxed configuration and into an installed configuration whereby the surgical staple compresses the one or more bones or bone pieces together.

11. The method of claim 10, wherein, in the installed configuration, the lower side of the bridge at the first and second extensions is abutting the one or more bones or bone pieces.

12. The method of claim 10, wherein the step of moving the surgical staple from the relaxed configuration to the tensioned configuration further comprises bending the bridge to a greater amount at the reduced width portion of the width of the bridge as opposed to i) between the first leg and the third leg; and i) between the second leg and the fourth leg when the surgical staple is moved from the relaxed configuration to the tensioned configuration.

13. The method of claim 10, wherein the step of moving the surgical staple from the relaxed configuration to the tensioned configuration further comprises:

contacting a side of the third leg facing the fourth leg with a first operative part of a spreading tool and contacting a side of the fourth leg facing the third leg with a second operative part of the spreading tool; and moving the first operative part of the spreading tool and the second operative part of the spreading tool away from each other to move the surgical staple from the relaxed configuration to the tensioned configuration.

14. The surgical staple of claim 1, wherein the upper side of the bridge includes a pair of lateral inclined surfaces on each side of the narrowed middle region of the smooth curved surface.

15. The surgical staple of claim 1, wherein the lower side of the bridge at the first and second extensions is, in use, abutting a bone and/or tissue.

16. The surgical staple of claim 1, wherein the first end of bridge and the second end of the bridge are each rounded such that the thickness is decreasing at the first end of the bridge and second end of the bridge.

17. A method of implanting the surgical staple of claim 1 into one or more bones or bone pieces, the method comprising:

drilling holes in the one or more bones or bone pieces for receiving the legs of the surgical staple;

moving the surgical staple from the relaxed configuration to the tensioned configuration;

inserting the legs of the surgical staple into the holes while the surgical staple is in the tensioned configuration; and allowing the surgical staple to move from the tensioned configuration toward the relaxed configuration and into an installed configuration whereby the surgical staple compresses the one or more bones or bone pieces together.

18. The method of claim 17, wherein, in the installed configuration, the lower side of the bridge at the first and second extensions is abutting the one or more bones or bone pieces.

* * * * *